(12) United States Patent
Spencer et al.

(10) Patent No.: US 6,500,363 B1
(45) Date of Patent: Dec. 31, 2002

(54) CLASSES OF HIGH LINEAR AND NONLINEAR RESPONSE COMPOUNDS

(75) Inventors: James T. Spencer, Fayetteville, NY (US); Damian G. Allis, Jamesville, NY (US)

(73) Assignee: Syracuse University, Syracuse, NY (US)

( * ) Notice: Subject to any disclaimer, the term of this patent is extended or adjusted under 35 U.S.C. 154(b) by 88 days.

(21) Appl. No.: 09/602,424

(22) Filed: Jun. 23, 2000

Related U.S. Application Data (60) Provisional application No. 60/141,343, filed on Jun. 28, 1999.

(51) Int. Cl.⁷ .................................................. G02B 1/00
(52) U.S. Cl. .............................. 252/582; 385/5; 556/8; 568/4; 568/3; 585/24; 252/587; 252/588; 252/589
(58) Field of Search ................ 385/5; 556/8; 568/4, 568/3; 585/24; 252/582, 587, 588, 589

(56) References Cited

U.S. PATENT DOCUMENTS

| | | | |
|---|---|---|---|
| 4,288,585 A | | 9/1981 | Allock et al. |
| 4,818,898 A | | 4/1989 | Anderson et al. |
| 4,859,876 A | * | 8/1989 | Dirk et al. |
| 4,962,979 A | | 10/1990 | Anderson et al. |
| 5,844,052 A | | 12/1998 | Keller et al. |

FOREIGN PATENT DOCUMENTS

JP 01291223 10/1989

OTHER PUBLICATIONS

Abe et al., Heterocyclic Betaines Exhibiting Extremely Large First Hyperpolarizability: Ab Initio and INDO/S Calculation, Journal of Amenican Chemical Society, vol. 118, 4707–4706 (1996).*
Harmon et al. Journal of the American Chemical Society, 89, 5309–5311 (1967).*
Yamaguchi et al, Bulletin of The Chemical Society of Japan, vol. 48(4), 1325–1326 (1975).*
Takahashi et al., Tetrahedron Letters, No. 50, 4655–46–58 (1976).*
Lee, S–G. et al., Synthesis of (ferrocenyl–indenyl) cyclopentadienyliron compounds with and without a bridging group via a CpFe transfer reaction. Inorganica Chimica Acta, Mar. 15, 1999, vol. 286, No. 2, pp. 215–220, especially pp. 218–219.

* cited by examiner

*Primary Examiner*—Robert Dawson
*Assistant Examiner*—Kuo Liang Peng
(74) *Attorney, Agent, or Firm*—Wall Marjama & Bilinski LLP (57) ABSTRACT

A class of molecules suitable for linear and nonlinear optical applications which include charged aromatic groups which function as electronic donors and acceptors connected through polyhedral and π-organic and inorganic groups. The polyhedral and π-organic and inorganic groups function as structural and electronic bridges for the charged donors and acceptors.

20 Claims, 7 Drawing Sheets

CLASSES OF HIGH LINEAR AND NONLINEAR RESPONSE COMPOUNDS

This application claims the benefit of provisional application Serial No. 60/141,343, filed Jun. 28, 1999.

BACKGROUND OF THE INVENTION

A critical aspect of the field of nonlinear optics (NLO) is focused upon the response of materials to electromagnetic fields. Interest often relates to how materials generate new electromagnetic fields with altered properties, such as frequency and phase, upon irradiation with an external electromagnetic field. Materials efficient at nonlinear photonic signal manipulation are of interest for a large number of technological applications including optical communications and computation, optical switching and limiting, data storage and retrieval, and dynamic image processing, among numerous others. (Prasad, P. R. and Williams, D. J. *Introduction to Nonlinear Optical Effects in Molecules and Polymers;* John Wiley and Sons: New York, 1991.) One of the primary limitations encountered, however, is the availability of suitable materials with large nonlinear responses. Most molecular nonlinear optical materials are inefficient photonic modulators. Major research initiatives have, therefore, been directed both toward gaining a detailed understanding of fundamental structure-optical property relationships and the theoretical modeling, experimental synthesis and NLO property measurement of new materials. A great deal of computational and experimental work, primarily with organic systems, has begun to address these important relationships. The present invention relates to the use of new classes of compounds as nonlinear optical materials.

Molecular NLO materials have many particularly attractive properties including ultrafast response times, lower dielectric constants, significantly improved processability, facile three dimensional design capabilities, and greatly enhanced NLO responses. (Blau, W. *Phys. Technol.* 1987, 18, 250.) Most molecular NLO materials, for example, employ electron donating (donors) and withdrawing groups (acceptors) connected through an organic framework (bridge), although several metalloorganic systems have also been explored. (Cummings, S. D., Cheng, L.-T. and Eisenberg, R. *Chem. Mater.* 1997, 9,440.)

The design and optimization of new NLO materials has primarily involved addressing what chemical factors affect the molecular hyperpolarizabilities of the material. For example, the most commonly employed model for understanding the fundamental relationships between the second-order responses ($\beta$) and molecular structure is the two-state model. (Oudar, J. L. *J. Chem. Phys.* 1977, 67, 446.) In qualitative terms, when the electric field component of a moderate strength incident electromagnetic wave interacts with a compound, a linear electronic polarization occurs within the compound due to photon-electron interactions. The incident oscillating electric field causes an oscillating dipole to be generated in the chromophore proportional to the applied field strength. At high incident field strength, however, the induced electronic polarization becomes nonlinear, ultimately leading to second, third, etc. harmonic generation. A power series expansion has been used to describe the nonlinear behavior of the induced polarization. In rigorously centrosymmetric chromophores, the second-order response is zero since only odd terms of the power series expansion are allowed. Molecular parameters which enhance a noncentrosymmetric electronic polarization in the compound, therefore, enhance its second-order response. For organic NLO materials involving electron donating and withdrawing groups (often referred to as "push-pull" systems), the value of $\beta$ is primarily dictated by the intramolecular charge polarization, the transfer integral and the excited state of the compound. The two-state model assumes that the large second-order response ($\beta$) is due primarily to an intramolecular charge-transfer interaction between the acceptor and donor portions of the material. The overall value of $\beta$ is given by the sum of an additive portion ($\beta_{add}$) and a charge transfer portion ($\beta_{ct}$). The additive portion ($\beta_{add}$) accounts for the interactions between the individual substituents and the organic framework. The dominant intramolecular electronic redistribution, or charge transfer contribution ($\beta_{ct}$), is given by:

$$\beta_{CT} = \frac{12\pi^2}{h^2} \frac{\omega_{max}}{(\omega_{max}^2 - 4\omega^2)(\omega_{max}^2 - \omega^2)} \eta_{ge}^2 \Delta\mu$$

(where $\omega_{max}$ is the absorption band maximum, $\omega$ is the frequency of the applied electric field, $\mu_{ge}$ is the transition dipole moment between the ground and lowest frequency excited state, and $\Delta\mu$ is the difference between the dipole moment of the ground and excited states). The two state model is a somewhat oversimplified description but it has been shown to be particularly useful in understanding the nonlinear optical properties of many molecular systems. Thus, in the "push-pull" organic compounds, increasing the length of the $\pi$-conjugated pathway between the donating and withdrawing groups and increasing the donor/acceptor group strengths typically leads to an increase in the observed electronic molecular hyperpolarizabilities. Increasing the length of the $\pi$-framework, however, also usually leads to a bathochromic shift of the intramolecular charge transfer absorption, typically into the visible region, which often limits the usefulness of the these materials. The calculated second-order responses for twisted $\pi$-chromophores, however, have been recently shown to be unresponsive toward the typical strategies for increasing $\beta$, such as by increasing both the length of the $\pi$-conjugation and the donor and acceptor strengths. This is primarily because the second-order responses for these twisted compounds are most dependent upon factors which effectively bring about and ultimately stabilize intramolecular charge separation. (Albert, I. D. L., Marks, T. J. and Ratner, M. A. *J. Am. Chem. Soc.* 1998, 120, 11174.).

The numeric values for $\beta$ range over six orders of magnitude, typically from about 0.001 for very small compounds to nearly 1000 ($\times 10^{-30}$ cm$^5$ esu$^{-1}$) for the best extended $\pi$-conjugated systems. Values of 10 to 100 (at 0.65 eV) are usually considered large and between 100 and 1000 ($\times 10^{-30}$ cm$^5$ esu$^{-1}$) exceptionally large. It is important to observe, however, that the magnitude of $\beta$ is rather sensitive to the frequency of the electromagnetic radiation employed and generally increases significantly with increasing excitation energy. In addition, these qualitative descriptions do not apply at near resonant frequencies. (Kanis, D. R., Ratner, M. A. and Marks, T. *J. Chem. Rev.* 1994, 94, 195). Table 1 gives several example molecular hyperpolarizabilities for known high $\beta$ NLO systems.

TABLE 1

Calculated and measured second-order responses ($\beta$) at 1.17 eV for selected high $\beta$ NLO compounds (aniline and nitrobenzene shown for comparison)[a]

| Compound | $\beta_{calc'd}$[b] | $\beta_{expt.}$ |
|---|---|---|
|  | 1.84 | 0.79–2.46 |

TABLE 1-continued

Calculated and measured second-order responses (β) at
1.17 eV for selected high β NLO compounds
(aniline and nitrobenzene shown for comparison)[a]

| Compound | $\beta_{calc'd}$[b] | $\beta_{expir.}$ |
|---|---|---|
|  | 4.55 | 1.97–4.6 |
|  | 34.4 | 16.2–34.5 |
|  | 213.1 | 180–260 |
|  | 466.8 | 470–790 |
|  | 30.8 | |

[a]The values of β are reported in units of $10^{-30}$ cm$^5$ esu$^{-1}$.
[b]Calculations are based upon the Pariser-Parr-Pople model.[24]

Calculational methods have been used to great effect in studying the relationships between nonlinear responses and molecular architectures. Numerous methods have been extensively and effectively employed including semiempirical methods (MOPAC and ZINDO principally), density functional theory (DFT) and ab initio methods. Significant advantages in calculational speed have been particularly realized by employing semiempirical methods (such as MOPAC AM1) which apparently retain the NLO calculational accuracy obtained with higher order ab initio basis sets (such as 6–31 G* *). Where experimental data exists, exceptionally good agreement is generally obtained between the calculated and experimental values of β as illustrated in Table 1.

OBJECTS OF THE INVENTION

A key component of research in NLO systems has involved the discovery of new materials efficient at nonlinear photonic signal manipulation. As described above, the value of β for molecular NLO materials is primarily determined by the intramolecular polarization, the transfer integral and the excited states of the compound. Chemical approaches designed to optimize these parameters by modifying the molecular architectures of the chromophore should directly result in increases in the observed nonlinear response. Several approaches have been developed for organic systems which have directly resulted in some observed increases in β for new materials (vide supra). It is apparent, however, that significantly better materials are yet possible. Since most of the known NLO materials are rather inefficient photonic modulators, it can clearly been seen that, in order for significant technological advances to be made in the use of NLO materials in opto-electronic and related applications, materials with significantly better NLO responses are required. In addition, current molecular NLO materials have significant problems associated with their chemical and thermal stability, processability, and synthetic facility. This invention describes new classes of compounds with both greatly enhanced NLO properties and significantly improved chemical and physical attributes.

SUMMARY OF THE INVENTION

Many types of molecular NLO compounds have been investigated, especially for the organic and metalloorganic-based systems. These studies have yielded incremental progress in new compounds with enhanced second-order responses. Thus far, little exploration has been directed toward either the application of molecular polyhedral-based systems or compounds with charged aromatic donor/acceptor moieties for NLO applications. (Grüner, B., Janousek, Z., King, B. T., Woodford, J. N., Wang, C. H., Vsetecka, V. and Michl, J. *J. Am. Chem. Soc.* 1999, 121, 3122; D. M. Murphy, D. M. P. Mingos, and J. M. Forward, *J. Mater. Chem.*, 1993, 3, 67; D. M. Murphy, D. M. P. Mingos, J. L. Haggitt, H. R. Powell, S. A. Westcott, T. B. Marder, N. J. Taylor, and D. R. Kanis, *J. Mater. Chem.*, 1993, 3, 139; J. Abe, N. Nemoto, Y. Nagase, Y. Shirai, and T. Iyoda, *Inorg. Chem.*, 1998, 37, 172). Polyhedral clusters provide a unique entry into a new class of high second-order response systems with significantly improved chemical and physical properties. Also, employing charged aromatic units as electronic donors and acceptors should significantly enhance NLO responses. Thus, this invention has arisen from the discovery that remarkably high calculated NLO responses were obtained from compounds based upon charged aromatic units serving as donors and acceptors (both inorganic and organic) connected through a variety of polyhedral and π-electron delocalized bridging groups (including organic groups, inorganic groups, aromatic groups, and olefinic groups). These classes of compounds show exceptionally high nonlinear responses (i.e., first hyperpolarizability, β second hyperpolarizability, γ, etc.), much larger than for other currently known compounds. In addition, these classes of compounds provide numerous other advantages. Thus, some of the principal features and advantages offered by these classes of compounds include, but are not limited to, the following;

(1) The use of charged aromatic groups (either organic or inorganic) or aromatic groups bearing charged substituents for the electronic donors and acceptors in nonlinear optical (NLO) materials.

(2) The use of polyhedral clusters and π-electron delocalized units (including π-aromatic units) as structural and electronic bridges for these donors and acceptors.

(3) The availability of three dimensional molecular structures, rather than the currently employed two-dimensional NLO structures, which allow for multiple donor and/or acceptor units per molecular unit and also allow for unique solid state and molecular arrays.

(4) The exceptional chemical and thermal stability of polyhedral subunits.

(5) The use of π-stacking interactions to facilitate self-assembly of the molecular NLO units into extended arrays (i.e., π-aromatic stacking).

(6) The use of inclusion and poled polymer compounds to facilitate the molecular alignment of the NLO chromophores.

(7) The incorporation of a wide variety of functional groups substituted on either or both the donor or acceptor groups and the bridge groups.

These features are summarized below.

Molecular main group polyhedra have several distinct advantages for NLO applications primarily arising from; (1) their synthetic availability and accessibility (with substitutional control), (2) the diversity of available three dimensional structural geometries and substitutional arrangements, (3) the extreme chemical and thermal stability of the polyhedral units, (4) the aromatic (or "pseudo" aromatic) electronic structures of the polyhedra with electron delocalized bonding arrangements, (5) their stability to photochemical and neutron irradiation ($^{10}$B capture cross section is 0.5±0.2 barnes), (6) the UV-visible and infrared features of polyhedral species which can be "designed" to display transitions ranging from the ultraviolet to the infrared, including visibly transparent species, and (8) the control of the structural, chemical and electronic properties of the materials.

Figure 1:
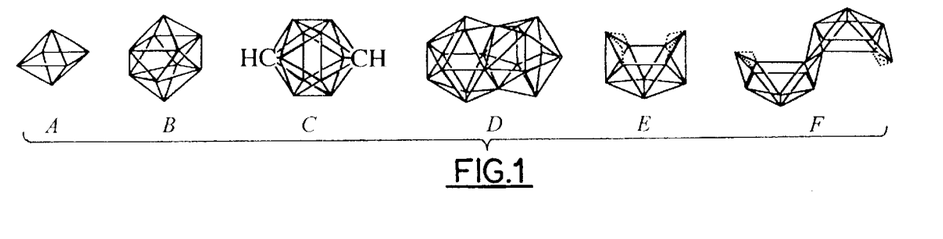
FIG. 1 illustrates examples of polyhedral systems which may be employed in compounds to provide enhanced NLO properties.

Among those features of main group polyhedra mentioned above, three in particular make them especially attractive for NLO materials. These are their stability, electronic properties and three dimensional structures. The closo-boranes and carboranes, for example, exhibit exceptional thermal and chemical stability. One of the polyhedra used here is the closo-1,12-$C_2B_{10}H_{12}$ framework which is thermally stable to well over 600° C. and is resistant to attack by boiling water and does not react with oxidizing agents, reducing agents or mineral acids. Larger linked $C_2B_{10}H_{12}$-based polymeric species have even shown thermal stability to long exposures at 600 to 1000° C. (Heying, T. L. Prog. Boron Chem. 1970, 2, 119). Part of this unique stability lies in the aromatic electron delocalization within the cluster framework. (Steudel, R. Chemistry of the Non-Metals deGruyter: Berlin, p. 375, 1977; Bamett-Thamattoor; Zheng, G., Ho, D. M. and Jones, M., Jr. Inorg. Chem. 1996, 35, 7311; Grimes, R. N. Carboranes; Academic: New York, pages 1–36, 1970). Molecular orbital descriptions of the bonding in these clusters bear close resemblance to a three dimensional benzenoid-like structure. This comparison is clearly seen in the actual reaction chemistry of $C_2B_{10}H_{12}$ which displays electrophilic and Friedel-Crafts reaction patterns very similar to that observed for benzene. Main group clusters display an incredible range of three dimensional structures, including species of exceptionally high symmetry, as illustrated by a few examples shown in FIG. 1. (Greenwood, N. N. and Earnshaw, A. Chemistry of the Elements Pergamon Press, Oxford, pages 174–207, 1985). All of these polyhedral frameworks (both those shown in FIG. 1 and those well known in the literature) are expected to display this same type of significantly enhanced NLO responses, although representative data is provided here only for selected examples.

Figure 2:
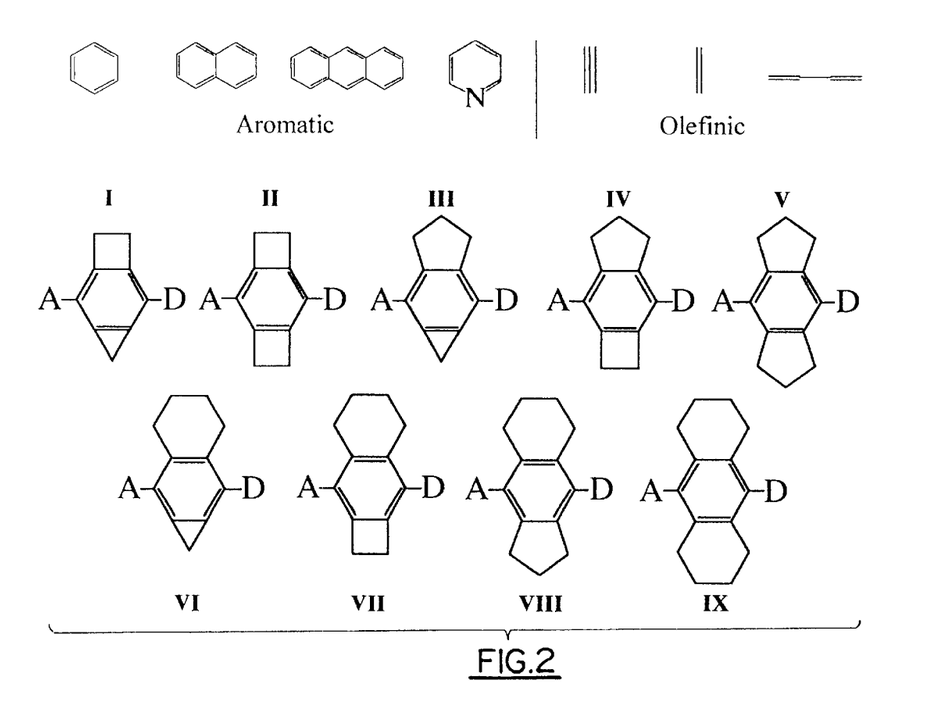
FIG. 2 illustrates examples of representative π-electron delocalized bridge systems which may be employed in compounds to provide enhanced NLO properties.

Electron delocalized organic bridges, when coupled with the charged aromatic donor and acceptor units described below, also show greatly enhanced NLO responses. These π-electron delocalized bridges include aromatic (i.e., phenyl, naphthyl, anthracenyl, hydrindacene, octahydroanthracene, pyridyl, etc . . . ) and olefinic bridges (ethylene, butadiene, acetylene, etc . . . ). Several representatives of these types of bridges are shown in FIG. 2.

Figure 3:
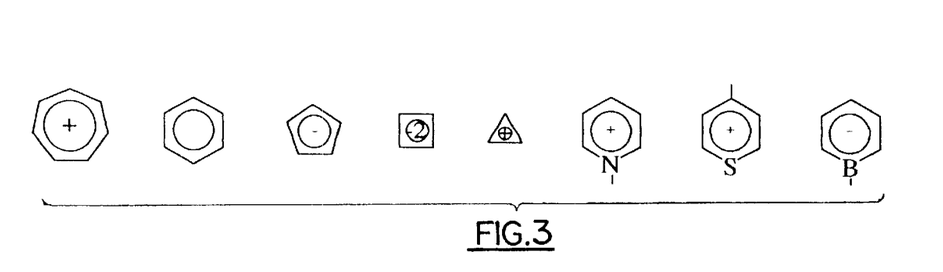
FIG. 3 illustrates examples of charged aromatic and π-electron delocalized groups which may be employed in compounds to provide enhanced NLO properties.

A second area of NLO enhancement described here comes through the use of aromatic donor and acceptor moieties. The donor and acceptor groups employed to date in NLO materials have primarily involved electronic redistribution through simple inductive effects, such as alkyl and amino groups for the donors and nitro and $SO_2CH_3$ groups for the acceptors. It should be possible, however, to greatly enhance the effect of the substituent groups on NLO parameters by employing appropriate aromatic systems, specifically groups such as the tropylium ($C_7H_7^+$) and cyclopentadienide ($C_5H_5^-$) which act both through inductive and aromatic π-stabilization effects. These, and the example related aromatic groups shown in FIG. 3, fulfill the Huickel 4n+2 rule for aromaticity. Based upon the data presented in the next section, the aromatic π-stabilization of these species is a major driving force to achieving very significant charge separation (localization) while providing for very large oscillator strengths. Also, neutral aromatic groups which themselves bear charged substituents, such as —$BR_3^{1-}$ and —$NR_3^{1+}$, give large calculated nonlinear responses. Further enhancements of the NLO responses are made by substituting various groups on the donor, acceptor or bridge units of the compound. Thus, by substituting methyl ($CH_3$) or amino groups ($NH_2$), for example, on the donor subunit, the NLO response is enhanced (vide infra). Similarly, by substituting groups such as $NO_2$ and COH, for example, on the acceptor subunit, the NLO response is again enhanced (vide infra). It is also important to note that the bridging group may also be substituted in a similar fashion.

This invention describes a novel class of molecular-based NLO material with greatly enhanced optical properties and significantly improved chemical and physical attributes over currently existing polyene and other π-delocalized molecular-based optical materials. This new family of material has direct use to a variety of applications including, but not limited to the following: optical communications and computation, optical switching and limiting, data storage and retrieval, dynamic image processing, frequency doubling, frequency upconversion, and four-wave degenerate mixing.

DETAILED DESCRIPTION OF THE INVENTION

Figure 4:
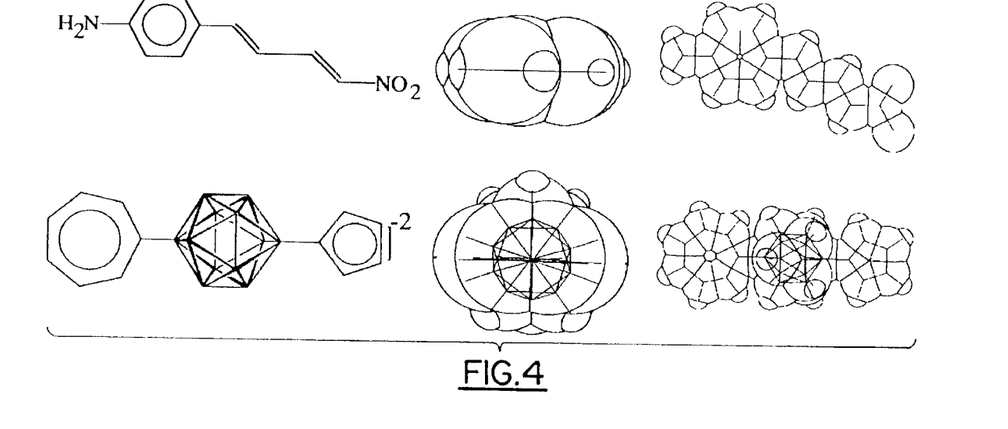
FIG. 4 illustrates a comparison between 1,4-[(NH$_2$)(C$_6$H$_4$)(CH=CHCH=CHNO$_2$)] (top) and 1,12-[(C$_7$H$_6$)B$_{12}$H$_{10}$(C$_5$H$_4$)]$^{-2}$ (bottom) using space filling models from MOPAC idealized geometries.

We have discovered through a quantum mechanical investigation of the linear and nonlinear responses of model compounds that the use of charged aromatic donor/acceptor moieties with molecular polyhedral and π-delocalized-based systems provides compounds with exceptional NLO responses. The model compounds described below employ very well known bridges and substitution patterns which may be derived through straightforward synthetic techniques established in the literature. A very wide range of polyhedral and π-delocalized bridges are, however, readily and straightforwardly available which should also provide for compounds with enhanced NLO properties (see FIG. 1). We similarly provide data here only for cyclopentadienide (Cp) and tropylium (Tp) donors and acceptors although many similar charged aromatic species are equally well suited to this application (see FIG. 3). Charged polyhedral species themselves, which may be thought of as either aromatic or pseudo-aromatic, may also be employed as the donors and acceptors besides as bridges. Finally, aromatic groups bearing charged substituents may also be used as donors and acceptors. It is entirely expected based upon literature precedent, however, that the scope and range of the cluster/π-delocalized bridges and donor/acceptor moieties possible are much larger than those illustrative examples discussed (vide supra). Thus, the compounds described below serve only as prototypes to provide concrete chemical architectural examples. Selected examples of representative species are given in Tables 2 and 3. The structures of polyhedra discussed here are based either upon closo-frameworks, such as $C_2B_{10}H_{12}$ and $B_{12}H_{12}^{-2}$, or upon more open nido-$B_{10}$ related framework structures. A typical example compound, $1,12-[(C_7H_6)B_{12}H_{10}(C_5H_4)]^{-2}$, is shown in FIG. 4 in comparison with the well known organic NLO chromophore, $4-[(NH_2)(C_6H_4)(CH=CHCH=CHNO_2)]$. The geometry of the planar Tp and Cp groups and the three-dimensional shape of the icosahedral cage is clearly evident in FIG. 4. It is noteworthy that the overall molecular dimensions of the polyhedral species are quite comparable with the $1,4-[(NH_2)(C_6H_4)(CH=CHCH=CHNO_2)]$ compound.

The work has also focused on gaining an understanding of both the magnitude and variation in the linear and nonlinear properties of new materials. From inspection of the results in Tables 2 and 3, it is clear that these prototypic new species have exceptionally large calculated β values. These values appear to be the among the largest ever reported. For example, the calculated β values for $1,12-[(C_7H_6)B_{12}H_{10}(C_5Me_4)]^{-2}$ ($\beta_{calc'd(0.5\ eV)}=1209\times10^{-30}$ cm$^5$ esu$^{-1}$) and $[(C_7H_6)B_{27}H_{28}(C_5Me_4)]$($\beta_{calc'd(0.5\ eV)}=8100\times10^{-30}$ cm$^5$ esu$^{-1}$) are more than 57 and 385 times larger, respectively, than that for the large extended π-conjugated "push-pull" organic compound $1,4-[(NH_2)(C_6H_4)(CH=CHCH=CHNO_2)]$($\beta_{calc'd(0.5\ eV)}=21\times10^{-30}$ cm$^5$ esu$^{-1}$) at 0.5 eV.

TABLE 2

Calculated second-order responses (β) at 0.5 eV for selected proposed NLO compounds[a,b]

| R | β[a] |
|---|---|

$1,12-[(C_7H_6)B_{12}H_{10}(R)]^{-2}$

| R | β[a] |
|---|---|
| R = $C_5H_4$ | 777.3 |
| R = $C_5Me_4$ | 1208.7 |
| R = $C_5Et_4$ | 1072.9 |
| R = $C_5(C_6H_5)_4$ | 365.9 |
| R =  | 685.6 |
| R =  | 647.0 |

$[(C_7H_6)C_4B_{20}H_{20}(R)]$

| R | β[a] |
|---|---|
| R = $C_5H_4$ | ~1000 |

TABLE 2-continued

Calculated second-order responses (β) at 0.5 eV for selected proposed NLO compounds[a,b]

| | R | $β^a$ |
|---|---|---|

[(C$_7$H$_6$)B$_{10}$H$_{12}$(R)]

R = C$_5$H$_4$    1029.8
R = C$_5$Me$_4$    1371.7

[(C$_7$H$_6$)B$_{27}$H$_{28}$(R)]

R = C$_5$H$_4$    5937.8
R = C$_5$Me$_4$    8413.9

[1,4-(C$_7$H$_6$)C$_6$H$_4$(R)]

R = C$_5$H$_5$    52.1
All co-planar
Perpendicular    383.1

[(C$_7$H$_6$)C$_2$B$_{10}$H$_{10}$(R)]

1,12 (para) isomer    681.9
R = C$_5$H$_4$    998.0
R = C$_5$Me$_4$    1063.5
R = C$_5$Et$_4$    18.4$^d$
1,2 (ortho) isomer
R = CH$_3$ (1,12-isomer shown)

TABLE 2-continued

Calculated second-order responses (β) at 0.5 eV for selected proposed NLO compounds[a,b]

| | R | $\beta^a$ |
|---|---|---|
| [(R)B$_{12}$H$_{10}$—C$_2$B$_{10}$H$_{10}$(R')]$^{-2}$  | R = R' = H<br>1,2-isomer[c]<br>1,7-isomer[c]<br>1,12-isomer[c]<br>R = Cp, R' = Tp<br>1,12-isomer<br>R = Tp, R' = Cp<br>1,12-isomer | 8.6<br>9.3<br>10.4<br>1226.0<br>158.3 |
| [(C$_7$H$_6$)B$_{18}$H$_{20}$(R)]  | R = C$_5$H$_4$<br>R = C$_5$Me$_4$ | 2914.7<br>4145.7 |
| [(C$_3$R'$_2$)B$_{12}$H$_{10}$(R)]$^{-2}$  | R = C$_5$H$_4$ R' = H<br>R = C$_5$Me$_4$ R' = H | 150.8<br>127.6 |
| [1,4-(NH$_2$)C$_6$H$_4$(NO$_2$)]  | | 5.3[a,f] 6.2[c]<br>16.2[e] |

[a]Calculated second-order responses (β) were completed using semi-empirical (MOPAC) calculations with AM1 parameterization at 0.5 eV using the E4 method. The values of β are reported in units of × 10$^{-30}$ cm$^5$ esu$^{-1}$.
[b]Shown for each compound is a MOPAC (AM1) optimized structure (top) and schematic line drawing (bottom). The terminal cage and tropylium hydrogens have been omitted from line drawings and cage borons are shown as unlabeled vertices.
[c]Literature β$_{(0)}$ values have been reported using ab initio calculations at 6-31G** for these compounds as; 1,12-[(B$_{12}$H$_{11}$)(C$_2$B$_{10}$H$_{11}$)]$^{-2}$ = 3.4, 1,7-[(B$_{12}$H$_{11}$)(C$_2$B$_{10}$H$_{11}$)]$^{-2}$ = 3.6, and 1,2-[(B$_{12}$H$_{11}$)(C$_2$B$_{10}$H$_{11}$)]$^{-2}$ = 3.6 × 10$^{-30}$ cm$^5$ esu$^{-1}$. For comparison, p-Nitroaniline had a β value of 6.2 × 10$^{-30}$ cm$^5$ esu$^{-1}$ using similar calculations (Abe, J.; Nemoto, N.; Nagase, Y.; Shirai, Y.; Iyoda, T. Inorg. Chem. 1998, 37, 172.)
[d]Known cationic compound (Harmon, K. M.; Harmon, A. B.; Thompson, B. C. J. Am. Chem. Soc. 1967, 89, 5309), although an experimental hyperpolarizability was not measured.
[e]Calculated with the Pariser-Parr-Pople model (PPP) at 1.17 eV (h/2π)ω field strength. References; (a) Zernike, F.; Midwinter, J. E. Applied Nonlinear Optics; John Wiley, New York, 1973; p. 41. (b) Li, D.; Ratner, M. A.; Marks, T. J. J. Phys. Chem. 1992, 96, 4325 and references therein.
[f]In comparison, the MOPAC calculated β value[a] for 1,12-[(NO$_2$)B$_{12}$H$_{10}$(NH$_2$)]$^{-2}$ is 2.1 × 10$^{-30}$ cm$^5$ esu$^{-1}$.

TABLE 3

Selected examples of calculated second-order responses (β) at 0.5 eV for selected proposed NLO compounds using π-delocalized bridges[a,b]

| | R | β[a] |
|---|---|---|
| Polyene [(C₇H₆)R(C₅H₄)]  (R = C₂H₂ shown) | R = C₂H₂<br>R = C₄H₄<br>R = C₆H₆<br>R = C₈H₈<br>R = C₁₀H₁₀ | 25.3<br>43.5<br>58.4<br>69.6<br>76.7 |
| Alkynyl [(C₇H₆)R(C₅H₄)]  (R = C₂ shown) | R = C₂<br>R = C₄<br>R = C₆ | 29.1<br>74.7<br>163.1 |
| Hindered Systems [substituted-octamethylanthracene]  | R = Me | 2947.0 |
| Complex [C₂₈H₂₂N₂]  | | 7225.0 |
| Benzene [(C₇H₆-(o,m,p)C₆H₄—C₅H₄)]  (1,4-isomer shown) | ortho (1,2)<br>meta (1,3)<br>para (1,4) | 12.7<br>−948.6<br>52.1 |
| Complex [(C₇H₆)R(C₅H₄)]  (R = (C₆H₄—C₂H₂) shown) | R = (C₆H₄—C₂H₂—C₆H₄)<br>R = (C₆H₄—C₄H₄—C₆H₄)<br>R = (C₆H₄—C₂H₂)<br>R = (C₂H₂—C₆H₄) | 237.7<br>283.8<br>84.5<br>87.9 |

TABLE 3-continued

Selected examples of calculated second-order responses (β) at 0.5 eV for selected proposed NLO compounds using π-delocalized bridges[a,b]

| R | β[a] |
|---|---|
| Hindered Systems [substituted-octamethylhydrindacene] | |
| R = Me | 4049.8 |
| R = Ph | 4701.8 |
| Complex [C₃₆H₂₄N₂] | 16697.3 |

[a]Calculated second-order responses (β) were completed using semi-empirical (MOPAC) calculations with PM3 parameterization at 0.5 eV field strength using the E4 method. The values of β are reported in units of × $10^{-30}$ cm$^5$ esu$^{-1}$.
Shown for each molecule is a schematic line drawing. The terminal hydrogens have been omitted from line drawings.

In order to begin to understand the effects of the ring substitutents on the hyperpolarizabilities, a series of compounds were calculated in which the bridge and charged ring identities remained constant while the ring substituent identities and substitution patterns were systematically changed. The data from these experiments are given in Tables 4 and 5. The calculated hyperpolarizabilities were found to be sensitive to both of these parameters with a four-fold increase in β observed relative to the unsubstituted system. Work in this area has also focused on exploring other cages, aromatic rings, ring substitutents and molecular geometries in order to optimize the responses of the compound and to gain a deeper understand of the mode of interaction among these various chemical parameters.

Figure 5:
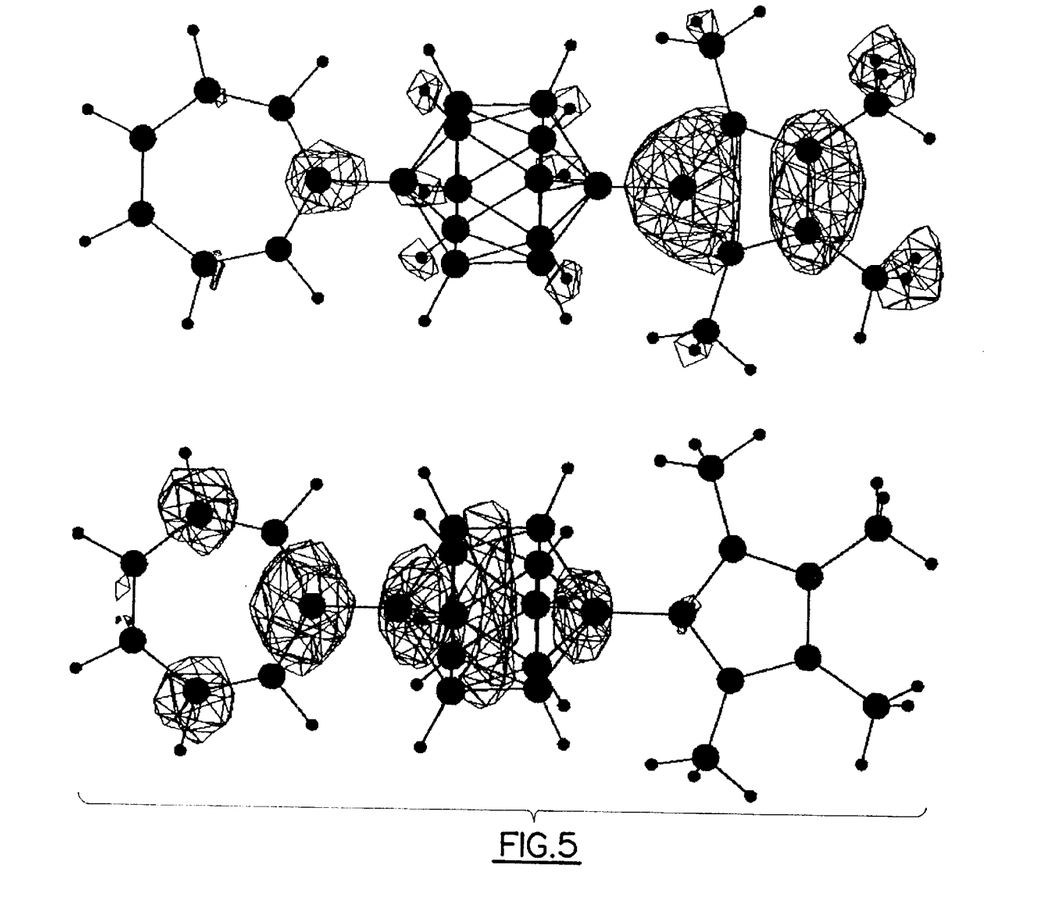
FIG. 5 illustrates calculated HOMO (left) and LUMO (right) molecular orbitals (MOPAC AM1) for 1,12-[(C$_7$H$_6$)B$_{12}$H$_{10}$(C$_5$Me$_4$)]$^{-2}$.

A partial understanding for the exceptionally large calculated responses for the new NLO systems may be gained by examining selected molecular orbitals for the NLO chromophores. The HOMO and LUMO are shown for a typical new compound, 1,12-[(C₇H₆)B₁₂H₁₀(C₅Me₄)]$^{-2}$, in FIG. 5. It appears that the ground state for these new systems may be described as two relatively independent, highly polarized regions. The HOMO, for example, is localized on the Cp ring while the LUMO is primarily located on the Tp ring. The transfer moment remains relatively large due to the electronic properties and three dimensional configuration of the polyhedron with a calculated oscillator strength of nearly 1.0. Increasing the charge separation between the organic rings and the polyhedron leads to substantial π-aromatic stabilization of both the tropyl and cyclopentadienyl subunits without introducing significant strain energy. Such an extremely large polarization coupled with a high oscillator strength would be expected to lead to the very large response properties observed. Distribution of the charge throughout the entire molecular system, in contrast, would lead to a diminution of the aromatic stabilization and greater conjugation between the polyhedron and the organic ring systems.

TABLE 4

Calculated β values as a function of substituent for 1,12-[(C₇R₄H₂)B₁₂H₁₀(C₅R'₄)]$^{-2}$ [a]

| R↓\R'→ | H | CH₃ | NH₂ | N(CH₃)₂ | OCH₃ |
|---|---|---|---|---|---|
| H | 777.3 | 1208.7 | 1366.3 | 1017.2 | 571.3 |
| F | 334.2 | 779.8 | 681.6 | 772.2 | 977.2 |
| Cl | 60.0 | 577.9 | 79.3 | 1453.1 | 1095.3 |
| CF₃ | 1080.2 | 1457.6 | 1513.4 | 1623.2 | 448.5 |
| NO₂ | 504.1 | 551.0 | 550.8[b] | 780.9 | 758.3 |
| COH | 1414.9 | 1862.1 | 2211.4 | 1217.5 | [c] |
| CN | 1339.0 | 1805.8 | 1875.8 | [c] | 677.5 |
| SO₂CH₃ | 382.0[b] | 446.1 | 469.2 | 473.3 | [c] |
| SO₂F | 224.3[b] | 248.0 | 245.8 | 211.0 | [c] |

[a]Calculated second-order responses (β) were completed using semi-empirical (MOPAC) calculations with AM1 parameterization of 0.5 eV field strength using the E4 method. The values of β are reported in units of −1 × $10^{-30}$ cm$^5$ esu$^{-1}$. The B₁₂H₁₀ cage unit in this comparative study was chosen both as a representative cluster and for calculational facility. Similar trends are expected for other cage geometries, structures and overall charge.
[b]The tropylium ring is slightly distorted from the planar configuration in the geometry optimized calculated structure.
[c]Not yet fully optimized structure (continuing work in progress)

TABLE 5

Calculated β values as a function of substitution pattern of the tropyl (Tp) and cyclopentadienyl (Cp) units in 1,12-[(Tp)(Cp)B$_{12}$H$_{10}$]$^{-2}$ compounds[a]

| Compound[a] | | Monosubstituted | |
|---|---|---|---|
| β | 777.3 | 860.7 | 948.3 |

| Compound[a] | Disubstituted | | Tetrasub. | Combined |
|---|---|---|---|---|
| β | 948.9 | 1086.6 | 1208.7 | 3368.1 |

| Compound[a] | | Monosubstituted | | |
|---|---|---|---|---|
| β | 777.3 | 634.0 | 67.6 | 1379.2 |

| Compound[a] | Disubstituted | | |
|---|---|---|---|
| β | 142.5 | 1339.0 | 2796.3 |

[a]Calculated second-order responses (β) were completed using semi-empirical (MOPAC) calculations with AM1 parameterization at 0.5 eV field strength using the E4 method. The values of β are reported in units of −1 × 10$^{-30}$ cm$^5$ esu$^{-1}$. The B$_{12}$H$_{10}$ cage unit in this comparative study was chosen both as a representative cluster and for calculational facility. Similar trends are expected for other cage geometries, structures and overall charge. For the calculations varying the substitution pattern of the cyclopentadienyl ring, the unsubstituted tropylium ring system (C$_7$H$_6$) was used. Similarly, for the calculations varying the substitution on the tropylium ring, the unsubstituted cyclopentadienyl ring system (C$_5$H$_4$) was employed. The methyl substitutents for the cyclopentadienyl ring and the cyano groups for the tropylium ring were chosen as representatives of ring substitution pattern effects. Similar trends are expected for other substitutents.

The absorption spectra of aromatic substituted polyhedral and electron delocalized bridge compounds are of interest relative to the potential applications of the material. The calculated UV-visible and infrared spectra for these types of compounds include colorless species and those which display very large infrared absorptions.

We have also explored the following items and found exceptionally high NLO responses; (1) use of higher level calculations (such as ab inito 6–31G**), (2) detailed examination of the molecular orbitals, charge distributions and related parameters, (3) exploration of coupled effects (such as employing charged aromatic substitution on the Tp and Cp groups themselves), and (4) internal angular dependence of NLO responses.

As with most currently employed NLO materials, attention must also be paid to developing materials which will form extended arrays in the solid phase, allowing for the development of solid state NLO materials which can be used in device fabrication. The use of aromatic π-stacking interactions as a method of structural stabilization is well documented in nature (i.e., in DNA and protein tertiary structures) and in the laboratory (i.e., in phenyl-perflourophenyl stacking interactions and some liquid crystal interactions). The source of this stacking stabilization comes from the electronic structure of the π-system, where noncovalent π-π interactions serve to electrostatically align the aromatic groups. The use of charged aromatic species in the design of these NLO materials provides an intrinsic method for the spontaneous self-assembly of extended π-stacked arrays. The n-stacking in these systems benefits appreciably from the use of charged aromatic species, as positively-charged and negatively-charged groups will preferentially stack in an ordered Coulombic fashion.

One important consideration in the application of new second-order NLO materials is the orientation of the chromophores, usually either on a surface or embedded within a substrate, such that a non-centrosymmetric arrangement is achieved. One molecular alignment method is based upon inclusion crystallization processes. Urea inclusion crystals, for example, form spontaneously in solution as helices of urea compounds. These helicies form around linear compounds, such as alkanes and mixed alkene-alkane species, encircling them in the urea channels. Because the urea solutions spontaneously self-assemble to form regular repeating structural features such as channels around long-chain organic systems, it should be possible to use these channels to align the NLO chromophores. Customization of the channel dimensions is possible by substitution of the urea, by the use of other urea derivatives, such as thiourea and selenourea, or by using other self-assembling compounds.

The cluster and polyene-based NLO chromophores are very well suited to fit within the channels of the urea lattice (channel van der Waals diameters range from 5.50 to 5.80 Angstroms in the urea compounds).

Another alignment method involves the use of poled-polymer and liquid crystal species to align and trap the NLO chromophores. The photopolymerization of long-chain organic compounds is well documented in literature, providing a variety of monomers that can be selected for their specific electronic and structural/thermal properties. The availability of a wide variety of monomers provides for the selectivity of polymer properties based on the need for such important operational characteristics as transparency in the UV-visible region and thermal stability. Further customization of the fmal polymer can be achieved by adjusting the relative proportions of chromophore to monomer, doping the chromophore/monomer mixture with other compounds (for changing the rigidity, thermal stability, or absorption characteristics), or by adding long-chain organic tails to the NLO chromophores themselves, embedding them further in the final polymer and adding to the rigidity of the final system.

In the following section, the experimental syntheses for several prototype compounds are presented as a natural extension of work presented above.

Synthesis of Prototype Polyhedral NLO Materials

Figure 6:
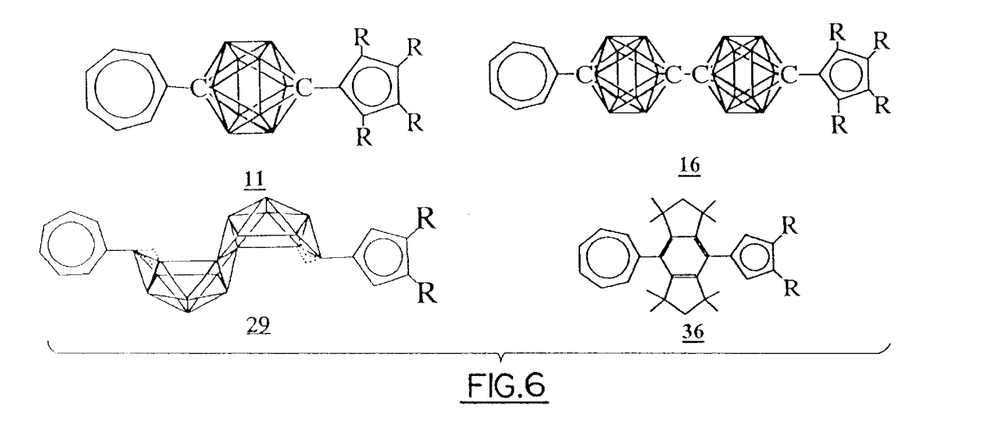
FIG. 6 illustrates selected new NLO compounds.

From our calculational work, four target compounds were selected for synthesis, both because of their expected direct synthetic approach from known compounds and reactions and due to their anticipated NLO properties. These target compounds are shown, along with their calculated β values, in FIG. 6. The pathways shown in this section serve to illustrate the approach using these well known literature techniques. The first two of these compounds, 11 and 16, are based upon the icosahedral closo-1,12-dicarbadodecaborane framework while compound 29 is based upon the more open nido-framework structures. (Spencer, J. T. In *The Encyclopedia of Inorganic Chemistry*, (King, R. B.; Burdett, J. K.; Wells, R.; Crabtree, R.; Sleight, A.; Scott, R.; Lukehart, C., Eds.); Wiley: New York, 1994, 538–557). The organic hydrindane compound, 36, is based upon the well known organic molecule. A brief synthetic overview for each of these target molecules is provided below.

The syntheses of the cluster-based compounds begin with either the icosahedral closo-1,12-$C_2B_{10}H_{12}$ or the nido-$B_{10}H_{14}$ clusters. These compounds are readily available, highly stable and easily handled in large scale using normal synthetic manipulations. Decaborane(17) is an air and water-stable solid at room temperature (v.p.$_{(60)}$=ca. 1 Torr) that was at one time manufactured on the multiton scale. ((a) Hurd, D. T. and Safford, M. M. U.S. Pat. No. 2,588,559 Jun. 26, 1954. (b) Safford, M. M. and Hurd, D. T. U.S. Pat. No. 2,588,561 Jun. 26, 1954. (c) Lipscomb, W. N. *Boron Hydrides*, Benjamin, N.Y. pages 1–275, 1963). The closo-1,12-$C_2B_{10}H_{12}$ starting compound has exceptional air, moisture and thermal stability (m.p.=260° C.) and is unreactive even towards concentrated mineral acids. ((a) Harmon, K. M., Harmon, A. B., Thompson, B. C., Spix, C. L., Coburn, T. T., Ryan, D. P. and Susskind, T. Y. *Inorg. Chem.* 1974, 13, 862. (b) Harnon, K. M., Nelson, T. E. and Stachowski, B. M. *J. Mol. Struct.* 1995, 350, 135. (c) Harmon, K. M., Harnon, A. B. and Thompson, B. C. *J. Am. Chem. Soc.* 1967, 89, 5309. (d) Harmnon, A. B. and Harmon, K. M. *J. Am. Chem. Soc.* 1966, 88, 4093. (e) Harmon, K. M., Harmon, A. B. and MacDonald, A. A. *J. Am. Chem. Soc.* 1969, 91, 323.) An extensive chemistry has been developed for both of these clusters. The known derivatives for the icosahedral dicarbadodecaboranes, for example, currently number well over 1400 compounds. ((a) Jothamn, R. W. "Carboranes" in *Mellor's Comprehensive Treatise on Inorganic and Theoretical Chemistry*, Vol. 5, Longman Press, London, 1974, pp 450. (b) Williams, R. E. "Carboranes" *Prog. Boron Chem.* 1970, 2, 37).

Figure 7:
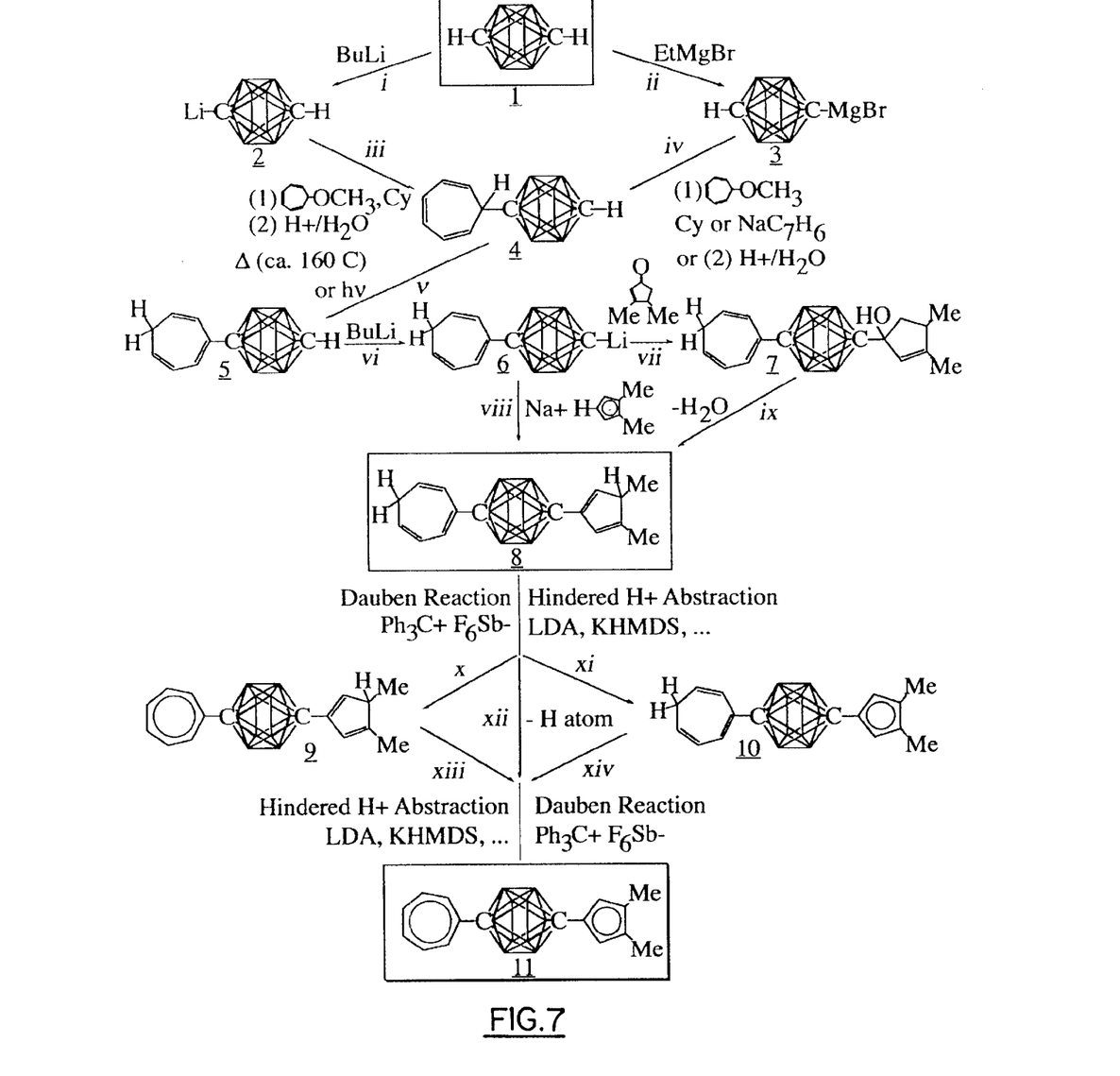
FIG. 7 illustrates synthetic routes to 1,12-[(C$_7$H$_6$)C$_2$B$_{10}$H$_{10}$(C$_5$H$_2$Me$_2$)] from 1,12-[C$_2$B$_{10}$H$_{12}$].
Figure 8:
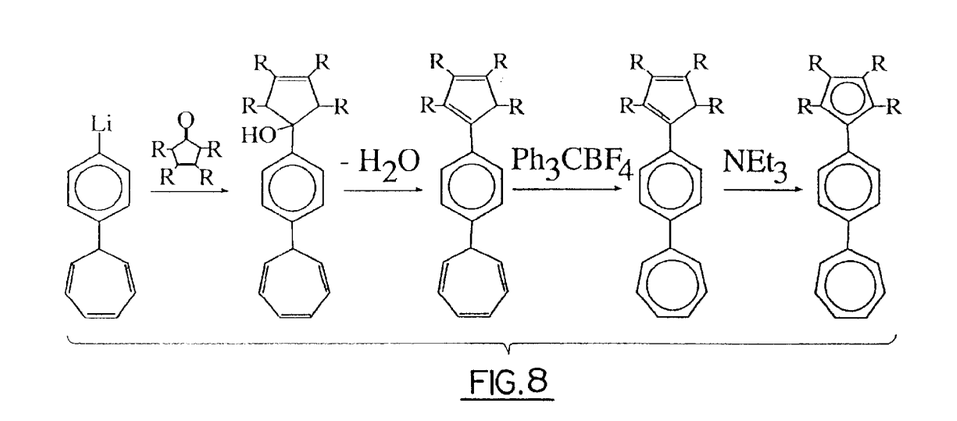
FIG. 8 illustrates a conventional synthetic route for the [5.6.7] quinarene system employed in the literature.

The synthesis of compound 11, shown in FIG. 7, is based upon the exceedingly stable closo-1,12-$C_2B_{10}H_{12}$ carborane cluster. In the first portion of the synthesis, the steps leading from 1,12-$C_2B_{10}H_{12}$ to the formation of compound 5 are essentially identical to those successfully employed in the high yield synthesis (93%) of the 1,2-[($C_7H_6$)($CH_3$) $C_2B_{10}H_{10}$]$^+$ cluster.[20] The reaction of butyl lithium with compound 5 then has provided a high yield pathway to the lithiated intermediate 6. The preferential site of lithiation at the cage C-H site in 5 is fully supported by calculational data which shows that the cage C-H proton is the only appreciably acidic hydrogen in compound 6. In addition, this cage C-H regiospecificity is also fully consistent with the literature synthesis of the direct organic analog p-tropylphenyllithium (FIG. 8) and the stability of the tropyl hydrogens in tropylcyclopentadienyl benzene derivatives toward lithiation by BuLi. (Niem, T. and Rausch, M. D. *J Org. Chem.* 1977, 42, 275; (a) Takahashi, K., Ookawa, I. and Takase, K. *Chem. Lett.* 1974, 1215. (b) Takahashi, K. and Takase, K. *Terahedron. Lett.* 1975, 245). Treatment of compound 6 with cyclopentenone followed by dehydration yields the key intermediate 8 in which both the tropyl and cyclopentadienyl units are substituted on the carborane framework. The reaction of 6 with cyclopentenone is directly analogous to the known reaction of cyclopentenone with p-tropylphenyllithium to yield the tropylphenylcyclopentadienyl carbinol, closely related to proposed carborane compound 7, as shown in FIG. 8. Cyano-group substitution on the cyclopentadiene ring may be performed here through reaction of 8 with ClCN. The final conversion of compound 8 to product 11 is accomplished through any of several routes involving a combination of a Dauben hydride and hindered $H^+$ abstraction reactions or radical or oxidative reactions well known in the literature, as illustrated shown for the [5.6.7]quinarene system. (Harmon, K. M. "Cycloheptatrienylium (Tropenylium) Ions" in *Carbonium Ions* by Olah, G. A.; Interscience Publ., New York 1973, 4, 1579).

Figure 9:
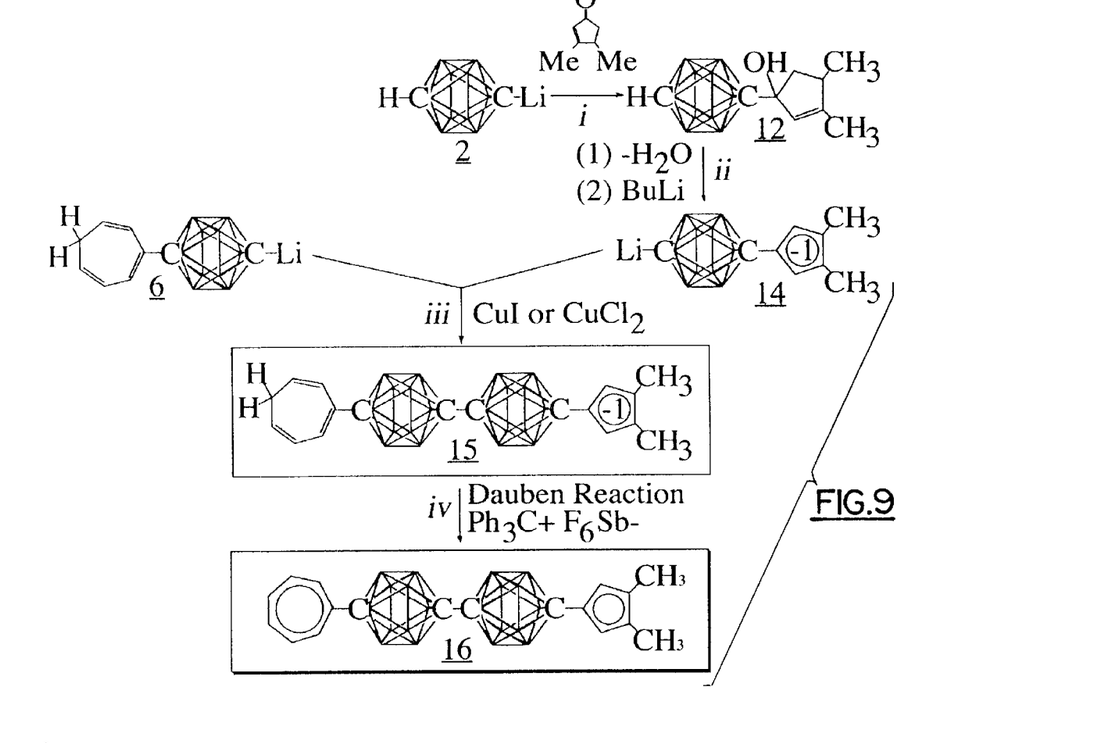
FIG. 9 illustrates synthetic routes to 1,12-[1-(C$_7$H$_6$)C$_4$B$_{20}$H$_{20}$-12'-(C$_5$H$_2$Me$_2$)].
Figure 10:
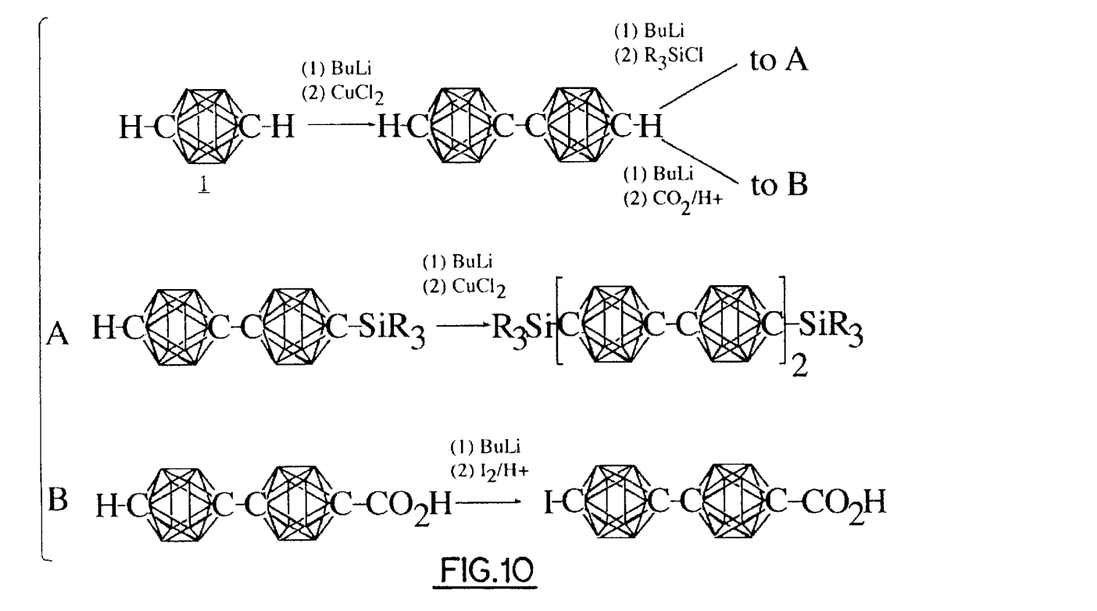
FIG. 10 illustrates a conventional synthetic route for the formation of dimeric and tetrameric rigid rod structures employed in the literature.

The synthesis of the second target compound, 16, is summarized in FIG. 9. The key step in the synthesis is the high yield metal catalyzed coupling of the two-cage substituted components 6 and 14. This type of coupling reaction is well known in cluster chemistry and has been used previously to successfully couple together substituted closo-$1,12$-$C_2B_{10}H_{12}$ units into dimeric, trimeric and tetrameric rigid rod ("carborod") structures (dimeric species prepared in 80% yield from closo-$1,12$-$C_2B_{10}H_{12}$), as shown in FIG. 10. ((a Müller, J., Base, K., Magnera, T. F. and Michl, J. *J. Am. Chem. Soc.* 1992, 114, 9721. (b) Yang, X., Jiang, W., Knobler, C. B. and Hawthorne, M. F. *J. Am. Chem. Soc.* 1992, 114, 9719. (c) Zakharkin, L. I. and Kovredov, A. I. *Izv. Akad. Nauk SSSR, Ser. Khim.* 1973, 1428). A similar approach has been previously employed in the synthesis of $IC_2B_{10}C_2B_{10}COOH$, as shown in FIG. 10. Once intermediate 15 has been generated, a simple Dauben reaction will generate the final product 16 in high yield.

Figure 11:
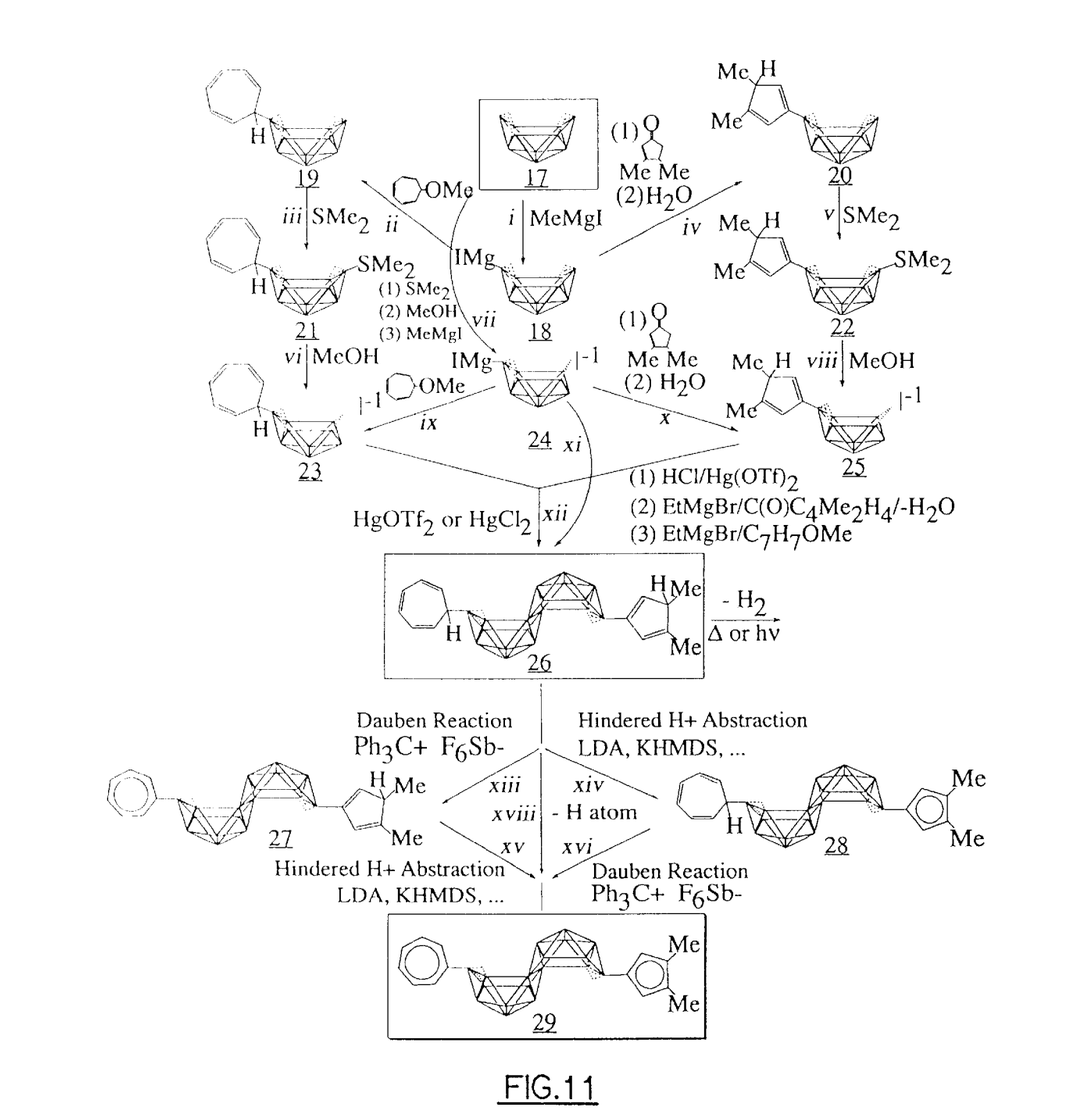
FIG. 11 illustrates synthetic routes to 9,9'-[(C$_7$H$_6$)B$_{18}$H$_{20}$(C$_5$H$_2$Me$_2$)] from decaborane(17).

The synthesis of compound, 29, is shown in FIG. 11. The starting point of this synthesis is the decaboranyl Grignard reagent 18. The metal promoted oxidative cage coupling reaction of 23 should generate 26 in high yield based upon literature reactions. (Gaines, D. F., Nelson, C. K. and Steehler, G. A. *J. Am. Chem. Soc.* 1984, 106, 7266). As in the previous syntheses, the final conversion of 26 to product 29 should be accomplished through any of several available routes. An alternative pathway may also be envisioned employing the initial fabrication of the unsubstituted $B_{18}$-framework followed by sequential tropyl and cyclopentadienyl ring substitution reactions to generate intermediate.

Figure 12:
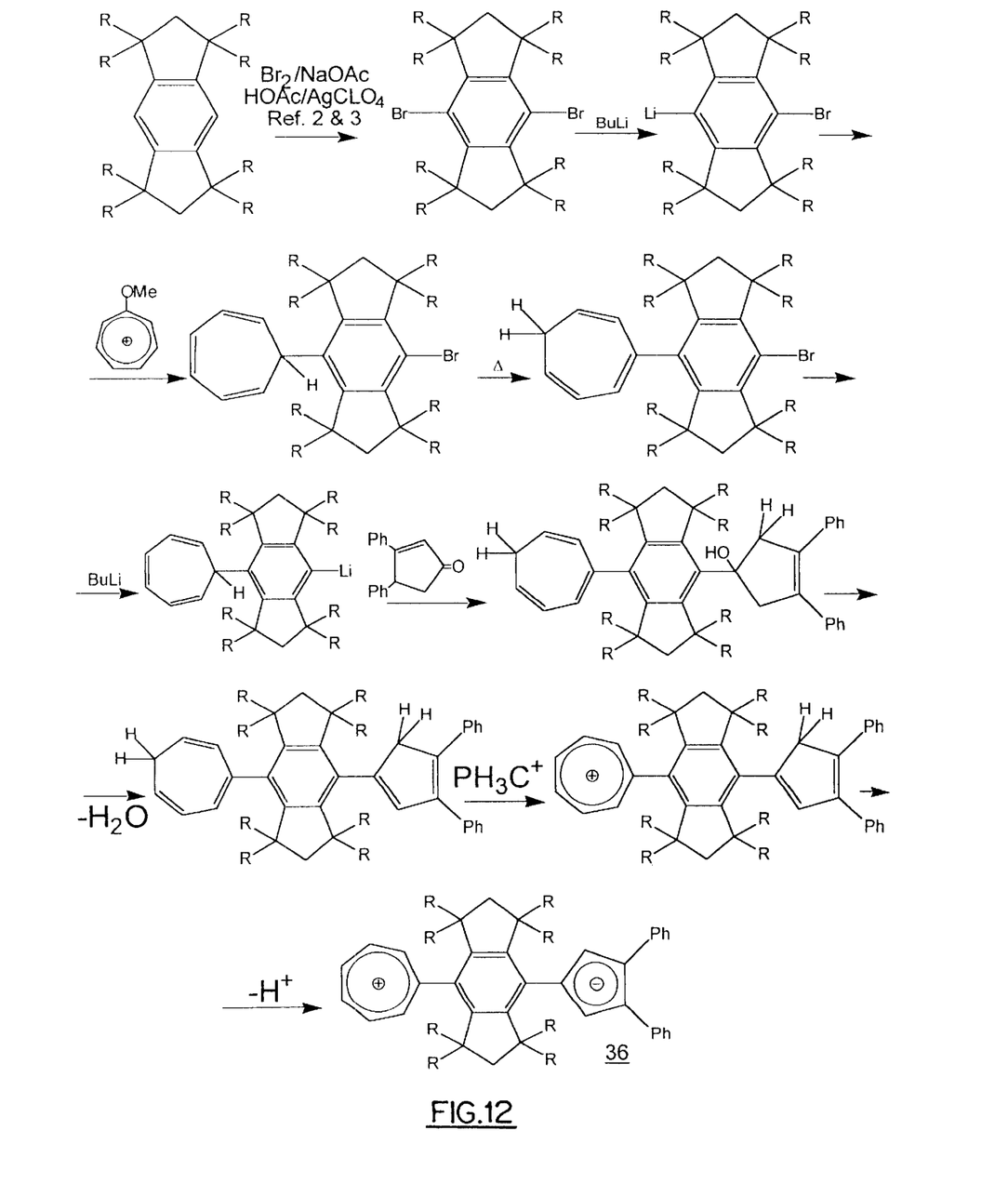
FIG. 12 illustrates synthetic pathways to the substituted octamethyl-hydrindacene compound.

Finally, the synthesis of the hydrindacene compound, 36, is outlined in FIG. 12.

While the specific embodiments of this invention have been illustrated and described herein, it is realized that straightforward modifications, changes, and logical extensions will occur to those skilled in the art. It is therefore to be understood that claims are intended to cover all modifications, changes and extensions that fall within the true spirit and scope of the invention.

We claim:

1. A compound suitable for linear and nonlinear optical applications which comprises charged aromatic groups which function as electronic donors and acceptors connected through polyhedral and/or π-aromatic and inorganic groups.

2. The compound of claim 1 in which the polyhedral and π-aromatic and inorganic groups function as structural and electronic bridges for said charged donors and acceptors.

3. A compound suitable for linear and nonlinear optical applications having the general formula: $[(C_7H_6^{-1})B_{12}H_{10}(R)]^{2-}$ where R is any one of $C_5H_4^{-1}$; $C_5Me_4^{-1}$; $C_5Et_4^{-1}$; $C_5(C_6H_5^{-1})_4$; $C_5(CN)_2Me_2^{-1}$; $C_5(CN)_3Me^{-1}$; $C_5(CN)_2Ph_2^{-1}$; or $C_5H_2Ph_2^{-1}$.

4. A compound suitable for linear and nonlinear optical applications having the general formula: $[(C_7H_6^+)C_4B_{20}H_{20}(R)]$ where R is $C_5H_4^{-1}$; $C_5Me_4^{-1}$; $C_5Et_4^{-1}$; $C_5(C_6H_5^{-1})_4$; $C_5(CN)_2Me_2^{-1}$; $C_5(CN)_3Me^{-1}$; $C_5(CN)_2Ph_2^{-1}$; or $C_5H_2Ph_2^{-1}$.

5. A compound suitable for linear and non-linear optical applications having the general formula: $[(C_7H_6^{+1})B_{10}H_{12}(R)]$ or $[(C_7H_6^{+1})B_{10}H_8(R)]^{2-}$ where R is $C_5H_4^{-1}$; $C_5Me_4^{-1}$; $C_5Et_4^{-1}$; $(C_5(C_6H_5)_4)^{-1}$; $C_5(CN)_2Me_2^{-1}$; $C_5(CN)_3Me^{-1}$; $C_5(CN)_2Ph_2^{-1}$; $C_5H_2Ph_2^{-1}$ or $C_5Me_4^{-1}$.

6. A compound suitable for linear and nonlinear optical applications having the general formula: $[(C_7H_6^{+1})B_{27}H_{28}(R)]$ where R is $C_5H_4^{-1}$; $C_5Me_4^{-1}$; $C_5Et_4^{-1}$; $(C_5(C_6H_5)_4)^{-1}$; $C_5(CN)_2Me_2^{-1}$; $C_5(CN)_3Me^{-1}$; $C_5(CN)_2Ph_2^{-1}$; $C_5H_2Ph_2^{-1}$ or $C_5Me_4^{-1}$.

7. A compound suitable for linear and nonlinear optical applications having the general formula: $[(C_7H_6^{+1})R(R')]$ where R is hydrindacene and R' is $C_5H_4^{-1}$; $C_5Me_4^{-1}$; $C_5Et_4^{-1}$; $(C_5(C_6H_5)_4)^{-1}$; $C_5(CN)_2Me_2^{-1}$; $C_5(CN)_3Me^{-1}$; $C_5(CN)_2Ph_2^{-1}$; or $C_5H_2Ph_2^{-1}$.

8. A compound suitable for linear and nonlinear optical applications having the general formula: $[(C_7H_6^{+1})C_2B_{10}H_{10}(R)]$ where R is any one of $C_5H_4^{-1}$; $C_5Me_4^{-1}$; $C_5Et_4^{-1}C_5(CN)_2Me_2^{-1}$; $C_5(CN)_3Me^{-1}$; $C_5(CN)_2Ph_2^{-1}$; $C_5(Ph)_4^{-1}$; and $C_2B_{10}H_{11}$.

9. A compound suitable for linear and nonlinear optical applications having the general formula: $(R)B_{12}H_{10}^{-2}$—$C_2B_{10}H_{10}(R')$ where R is $C_7H_6^{+1}$ and R' is $C_5H_4^{-1}$, $C_5Me_4^{-1}$, or H; or where R is $C_5H_4^{-1}$, $C_5Me_4^{-1}$, or H and R' is $C_7H_6^{+1}$.

10. A compound suitable for linear and nonlinear optical applications having the general formula: $[(C_7H_6^{+1})B_{18}H_{20}(R)]$ where R is any one of $C_5H_4^{-1}$ and $C_5Me_4^{-1}$.

11. A compound suitable for linear and nonlinear optical applications having the general formula: $[(C_3R'_2)B_{12}H_{10}(R)]^{2-}$ where R is $C_5H_4^{-1}$ and R' is H; or where R is $C_5Me_4^{-1}$ and R' is H.

12. A compound suitable for linear and nonlinear optical applications having the general formula: $[1,4$-$(NH_2)C_2B_{10}H_{10}(NO_2)]$.

13. A compound suitable for linear and nonlinear optical applications having the general formula: $[(C_7H_6)R(R')]^n$ (where n is 0 or −1) where R is based on either unsubstituted or substituted variant species of cyclopropa[4,5]benzocyclobutene; benzo[1,2:4,5]dicyclobutene; tetrahydrocycloprop[f]indene; 4,5-cyclopentenobenzocyclobutene; octahydrohydrindacene; tetrahydrocyclopropa[b]naphthalene; hexahydrocyclobuta[β]naphthalene; tetrahydrobenzindane; and octahydroanthracene and R' is any one of $C_5H_4^{-1}$; $C_5Me_4^{-1}$; $C_5Et_4^{-1}$; $C_5Ph_4^{-1}$; $C_5H_2Ph_2^{-1}$; $C_5H_2Me_2^{-1}$; $C_5H_3Me^{-1}$; $C_2B_{10}H_{11}$; $CH_3$; $C_5(CN)_2Me_2^{-1}$; $C_5(CN)_3Me^{-1}$; $C_5(CN)_2Ph_2^{-1}$; $BC_5H_5^{-1}$; $C_6Me_3H_2$; $NH_2$; and $NMe_2$.

14. A compound which exhibits enhanced NLO properties which employs aromatic units which serve as donors and acceptors which are connected through polyhedral and/or π-electron delocalized bridging groups, wherein said donors, acceptors and bridging groups comprise:

(a) donors selected from the group consisting of $C_5H_4^{-1}$; $C_4H_3^{-2}$; $BC_5H_5^{-1}$; $B_{10}H_9^{-2}$; $B_{12}H_{11}^{-2}$; $CB_9H_9^{-1}$; $CB_{11}H_{11}^{-1}$; $C_2B_4H_5$; $C_2B_8H_9$; $C_2B_{10}H_{11}$; $B_{10}H_{13}$; and $B_5H_8$;

(b) acceptors selected from the group consisting of $C_7H_6^{+1}$; $C_3H_2^{+1}$; $NC_5H_5^{+1}$; $SC_5H_4^{+1}$; $FeCp_2$; $Fe(CO)_n$ (where $_n=1, 2, 3, 4$); FeCp(CO)$_2$; B$_5$H$_4^{-2}$; B$_6$H$_5^{2-}$; B$_{12}$H$_{12}^{2-}$; C$_2$B$_4$H$_5$; C$_2$B$_8$H$_9$; C$_2$B$_{10}$H$_{11}$; B$_{10}$H$_{13}$; B$_5$H$_8$; and

(c) bridge groups selected from the bridge groups in borane polyhedral compounds, carborane polyhedral compounds and π-aromatic compounds as shown in I through IX:

I

II

III

IV

V

VI

VII

VIII

IX wherein A is an acceptor, and D is a donor.

15. The compound of claim 14 in which the hydrogens of groups of the donor are substituted by other groups to enhance donor properties or crystal orienting properties.

16. The compound of claim 14 in which the hydrogens of groups of the acceptor are substituted by other groups to enhance acceptor properties or crystal orienting properties.

17. The compound of claim 14 in which the hydrogens of groups of the bridge are substituted by other groups to enhance bridge properties or crystal orienting properties.

18. The compound of claim 15 in which the substituted group is at least one selected from the group consisting of methyl, ethyl, propyl, butyl, pentyl, cyclohexyl, phenyl, naphthyl, indenyl, fluorenyl, NH$_2$, NMe$_2$, NEt$_2$, OMe, OEt, CN, COH and F.

19. The compound of claim 16, in which the substituted group is at least one selected from the groups consisting of halogens, CF$_3$, C$_2$F$_5$, NO$_2$, aldehydes, esters, carboxylic acids, ketones, CN, SO$_2$CH$_3$, SO$_2$F, CH$_3$, C$_2$H$_5$ and NH$_2$.

20. The compounds of claim 17 in which the substituted group is at least one selected from the group consisting of methyl, ethyl, propyl, butyl, pentyl, cyclohexyl, phenyl, naphthyl, indenyl, fluorenyl, NH$_2$, NMe$_2$, NEt$_2$, OMe, OEt, halogens, CF$_3$, C$_2$F$_5$, NO$_2$, aldehydes, esters, carboxylic acids, kentones, CN, SO$_2$CH$_3$ and SO$_2$F.

* * * * *